United States Patent [19]

Gysin et al.

[11] Patent Number: 5,714,105
[45] Date of Patent: Feb. 3, 1998

[54] METHOD OF MAKING AN ENDOPROSTHESIS OF COMPACT THERMOPLASTIC COMPOSITE MATERIAL

[75] Inventors: Hansjörg Gysin; Robert Michael Streicher, both of Winterthur, Switzerland

[73] Assignee: Sulzer Medizinaltechnik, Winterthur, Switzerland

[21] Appl. No.: 345,659

[22] Filed: Nov. 28, 1994

Related U.S. Application Data

[63] Continuation-in-part of Ser. No. 65,311, May 21, 1993, abandoned.

[30] Foreign Application Priority Data

Jun. 4, 1992 [EP] European Pat. Off. ............ 92 810432

[51] Int. Cl.⁶ ..................... B29C 43/18; B29C 43/52
[52] U.S. Cl. ............ 264/257; 264/258; 264/136; 264/137
[58] Field of Search ................. 264/275, 257, 264/258, 259, 134, 135, 136, 137, 109, 113, 119, 125, 128

[56] References Cited

U.S. PATENT DOCUMENTS

| 3,886,600 | 6/1975 | Kahn . |
| 3,893,196 | 7/1975 | Hochman . |
| 4,089,071 | 5/1978 | Kalnberz . |
| 4,454,612 | 6/1984 | McDaniel . |
| 4,506,681 | 3/1985 | Mundell . |
| 4,714,467 | 12/1987 | Lechner . |
| 4,902,297 | 2/1990 | Devanathan . |
| 4,927,581 | 5/1990 | Medwin ................ 264/257 |
| 4,986,948 | 1/1991 | Komiya et al. ........ 264/257 |
| 5,041,260 | 8/1991 | Johnson et al. ....... 264/257 |
| 5,192,330 | 3/1993 | Chang .................... 623/18 |
| 5,424,017 | 6/1995 | Hinduja et al. ........ 264/328.7 |

FOREIGN PATENT DOCUMENTS

| 3613657 | 11/1987 | Germany . |
| 2 216 425 | 11/1989 | United Kingdom . |

*Primary Examiner*—Angela Y. Ortiz
*Attorney, Agent, or Firm*—Townsend and Townsend and Crew, LLP

[57] ABSTRACT

An endoprosthesis of compact thermoplastics including composite materials is disclosed. The endoprosthesis includes a plurality of prefabricated fibers such as carbon or aramid. Thermoplastics such as polyacrylates, polyaryl ether ketones, polycarbonates, polyether sulphones, polyethylenes or polyproplyenes are used as a binding agent. The prefabricated fibers have an internal core with predominately longitudinally oriented fibers and an enclosing covering with mutually intersecting fibers. The prefabricated fibers are cut to a length which is preferably five times their minimum diameter. The fibers are oriented substantially parallel to the major axis of the endoprosthesis. During molding and even in shallow cross-sections relative to the major axis of the endoprosthesis, each prefabricated fiber is at least partially overlapped by an adjoining prefabricated fiber. It is preferred that the prefabricated fibers at their ends take various forms including tapering, bevelled, and may have scooped, spherical or dished areas. A compression mold is used. The compression mold defines a female cavity which contains the elongate male profile of the endoprosthesis. Preheated prefabricated fibers are placed into the compression mold of the endoprosthesis. The fibers are all generally parallel to the major axis of the mold. Relative to cross-sections taken across the major axis of the mold, the number and array of the fibers varies as the particular cross-section varies. Specifically, at large cross-sections many fibers are found; at small cross-sections, the fibers are reduced in number.

2 Claims, 4 Drawing Sheets

METHOD OF MAKING AN ENDOPROSTHESIS OF COMPACT THERMOPLASTIC COMPOSITE MATERIAL

This application is a continuation-in-part of Ser. No. 08/065,311, filed May 21, 1993, now abandoned.

BACKGROUND OF THE INVENTION

The problem underlying the present invention is to create an endoprosthesis with a structure which is simple and reliable to produce, and which exhibits throughout high specific mechanical resistance to tension, bending and torsion and very good long term rupture strength. Above all, mechanical weak points should also be eliminated. This problem is solved by an endoprosthesis according to the invention which utilizes thermoplastic mold in combination with composite materials in the form of fibers cured within a mold.

The problem with long fibers in a thermoplastic mold is that it is very difficult to obtain uniform distribution of the fibers when filling a mold. This is especially true where the mold has varying cross-sectional areas over a major axis of the formed article.

Two technical solutions have been offered. In a first known method, parts of constant cross-sectional area having a uniform distribution of fibers are produced. Afterwards, the formed material is machined to the desired shape.

In a second known method, a mold is filled in a layered manner—either with discrete fibers or material having fibers woven and/or unidirectionally laid in discrete layers. Thereafter, the discrete layers are pressed and heated effecting curing of the finished article.

SUMMARY OF THE INVENTION

An endoprosthesis of compact thermoplastics including composite materials is disclosed. The endoprosthesis includes a plurality of prefabricated fibers such as carbon or aramid. Thermoplastics such as polyacrylates, polyaryl ether ketones, polycarbonates, polyether sulphones, polyethylenes or polyproplyenes are used as a binding agent. The prefabricated fibers have an internal core with predominately longitudinally oriented fibers and an enclosing covering with mutually intersecting fibers. The prefabricated fibers are cut to a length which is preferably five times their minimum diameter. The fibers are oriented substantially parallel to the major axis of the endoprosthesis. During molding and even in shallow cross-sections relative to the major axis of the endoprosthesis, each prefabricated fiber is at least partially overlapped by an adjoining prefabricated fiber. It is preferred that the prefabricated fibers at their ends take various forms including tapering, bevelled, and may have scooped, spherical or dished areas.

A compression mold is used. The compression mold defines a female cavity which contains the elongate male profile of the endoprosthesis. Preheated prefabricated fibers are placed into the compression mold of the endoprosthesis. The fibers are all generally parallel to the major axis of the mold. Relative to cross-sections taken across the major axis of the mold, the number and array of the fibers varies as the particular cross-section varies. Specifically, at large cross-sections, many fibers are found; at small cross-sections, the fibers are reduced in number.

Once the mold is filled, the fibers are compacted under heated compression within the mold. The placed fibers move and conform relative to one another and the walls of the mold. Such movement and conformation occurs until all areas of the mold are filled. There results a solid cured unitary article with aligned fibers as a result of this process.

It is important to note that the article can be fully formed by this process to its desired shape. It is not necessary to machine or otherwise process that article to obtain the desired shape.

This technique can be advantageously used for forming the stem of a femur prothesis. The conforming movement of the fibers during compression molding and the finish of the ultimately produced endoprosthesis become better when the respective fibers are cut at their respective ends with a bevel relative to their major axis as distinguished from parallel to their major axis. Although the respective fiber pieces have a length and bevel cut which is essentially uniform, it has been found that the varying cross-sections required in the endoprosthesis are easily formed. Further, even though the cross-section of the prothesis may vary widely along the major axis, uniform strength results. This uniform strength results from the substantially uniform distribution of fibers and thermoplastic along the formed endoprosthesis.

The inherently stable elongated elements, their intimate connection to one another and their alignment along the preferred directions produce structures with particularly good specific resistance values for tension, compression and torsion. In addition local weak points are thereby largely eliminated, even with complicated shapes.

Advantageous developments of the structures in accordance with the invention are also disclosed. For example, the elongated elements may have a unidirectional core or a core comprising an elongated braid with a small fibre angle. The enclosing cover may be formed in a simple manner from mutually intersecting layers or a braid. Particularly satisfactory mechanical properties can be obtained with highly compacted functional parts having a proportion of voids of at most 1%. Particularly suitable thermoplastics may be: polyacrylates, polyaryl ether ketones, polycarbonates, polyether sulphones, polyethylenes or polypropylenes. Suitable fibers may be of carbon or aramid.

Depending on the shape of the endoprosthesis it may be possible to obtain particularly satisfactory mechanical properties with elongated elements of which the length is at least five times their minimum diameter, or with elongated elements of which the ends finish obliquely and so produce a more intimate connection with adjoining elongated elements. The elongated elements may be continuous through the endoprosthesis along their entire length, that is, may end only at its surfaces. It is preferred that the length of the fibers be less than half the length of the main dimension of the product along the major axis. Advantageously all elongated elements, even in flatter parts of the endoprosthesis, are at least partly overlapped by an adjoining elongated element, and at least 6 elongated elements may lie within a primary cross-section. The functional parts according to the invention may take various forms: they may dwindle to nothing at one end or be bevelled, and they may have scooped, spherical or dished areas.

With the structure according to the invention it is also possible, above all, to form endoprosthesis which are exposed to high mechanical stresses. Particularly stable endoprostheses may have a stem for implantation in a tubular bone, or they may form a stem which ends in a cup or a rounded head. By thermoplastically installing a metal mesh on the surface, and by anchoring in the surface, it is possible to achieve a particularly satisfactory connection to the surrounding bone material or the bone cement. In addition radiation markers may be built into the endoprosthesis of composite material at predetermined points for the purpose of post-operative monitoring of the position of the prosthesis relative to the bone.

BRIEF DESCRIPTION OF THE DRAWINGS

The invention will now be described in more detail with reference to examples and figures, in which.

DESCRIPTION OF THE PREFERRED EMBODIMENT

Figure 1A:
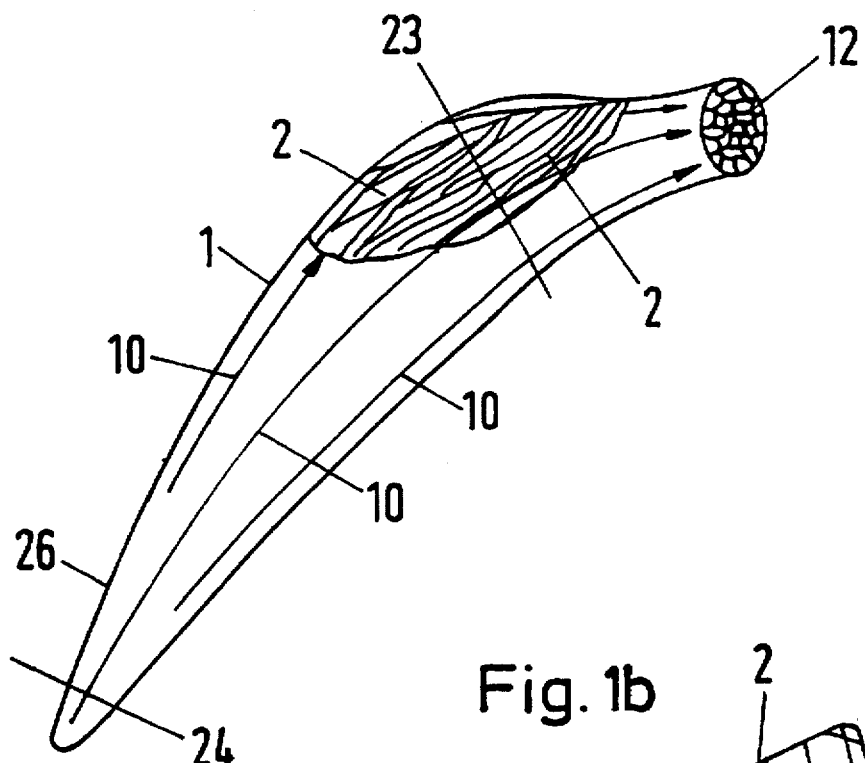
FIGS. 1A, 1B, 1C illustrate an endoprosthesis embodying the invention, comprising compacted elongated elements and the structure of these elements.
Figure 1B:
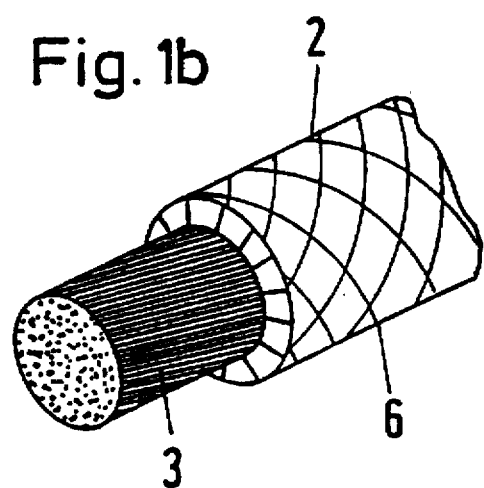
Figure 1C:
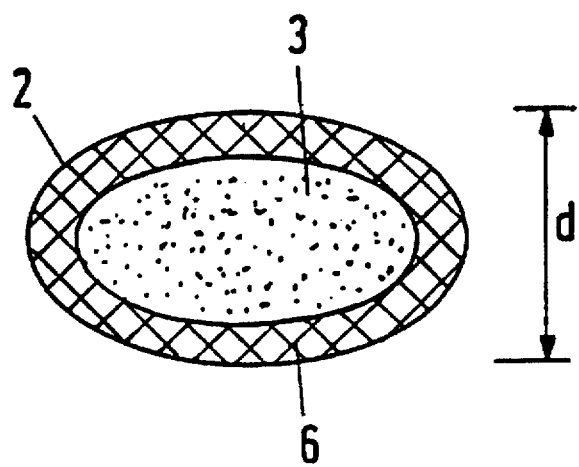
Figure 2:
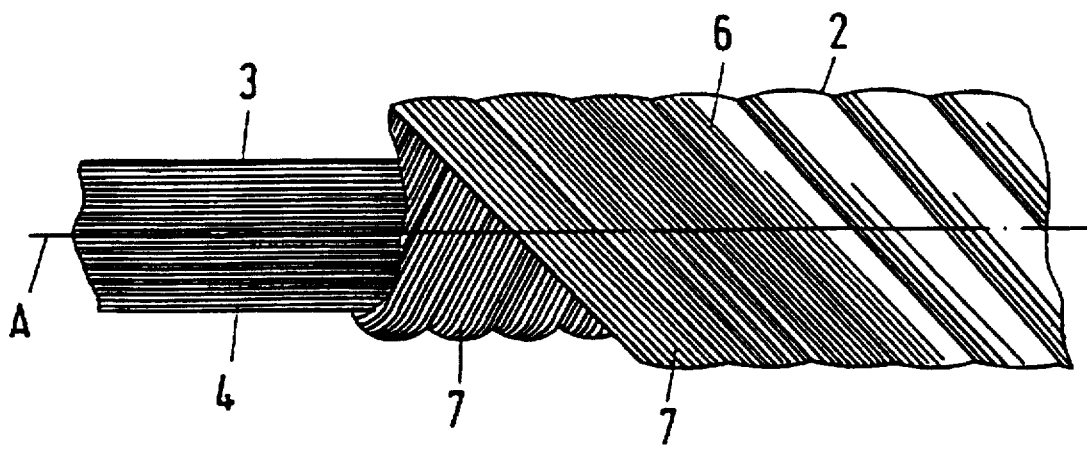
FIGS. 2, 3 show examples of elongated elements with an internal core and covering.
Figure 3:
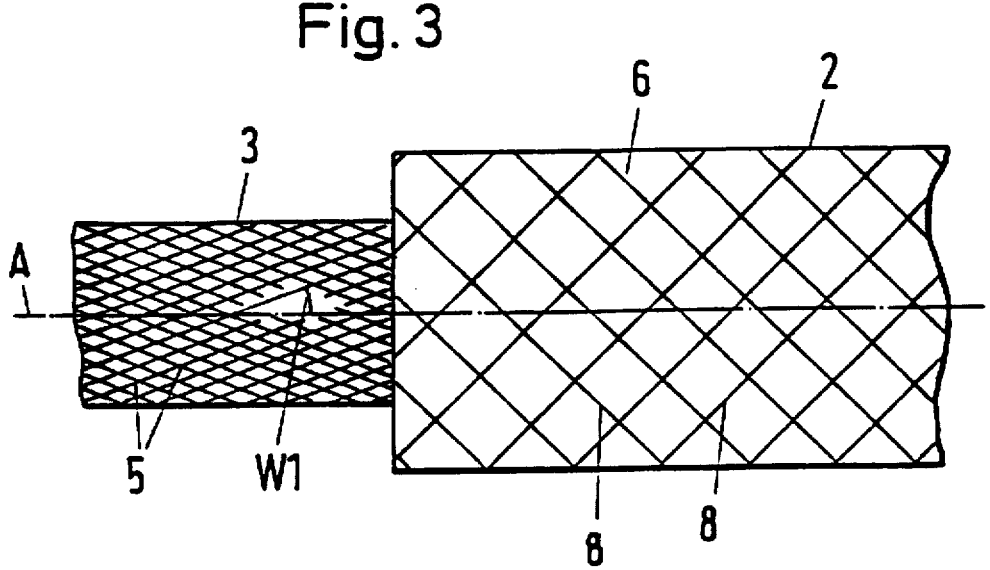

FIG. 1A shows an endoprosthesis with a tapering end 26. The endoprosthesis comprises compacted elongated elements 2 which at all points are oriented along a preferred direction 10 and are mutually connected thermoplastically over their entire length. The preferred directions 10 here run from one end surface 12 to the end 26. The shape and size of the cross-section changes in the preferred direction 10 or over the functional part 1 from a small cross-section 24 on the tapering end 26 to a larger, altered cross-section 23 in the upper part of the endoprosthesis. The elongated elements 2 (shown in FIG. 1B, or in cross-section in FIG. 1C) have an internal core 3 with predominantly longitudinally oriented fibers and an enclosing covering 6 with mutually intersecting fibers. FIG. 1C illustrates an oval cross-section with a minimum diameter D. The elongated element 2 in the example in FIG. 2 has a unidirectional core 4 surrounded by two crossing superjacent layers 7. In FIG. 3 the core comprises an elongated braid 5 with a maximum fibre angle W1 of 20° to the element axis A. The enclosing covering 6 comprises a braid 8 with a relatively large fibre angle of, for example, 35 to 45°. In the case of the layer 7 this fibre angle may be even greater, for example 45° to 55°. With the structure according to the invention comprising elongated elements 2 with a longitudinally oriented core and highly crossing covering fibers it is possible to produce in a simple manner endoprostheses with an extremely wide range of shapes and with excellent mechanical strength and torsion properties throughout the volume of the endoprosthesis, and without weak points. The elimination of weak points is particularly important in endoprostheses of composite materials, and is also correspondingly difficult to achieve.

Figure 4:
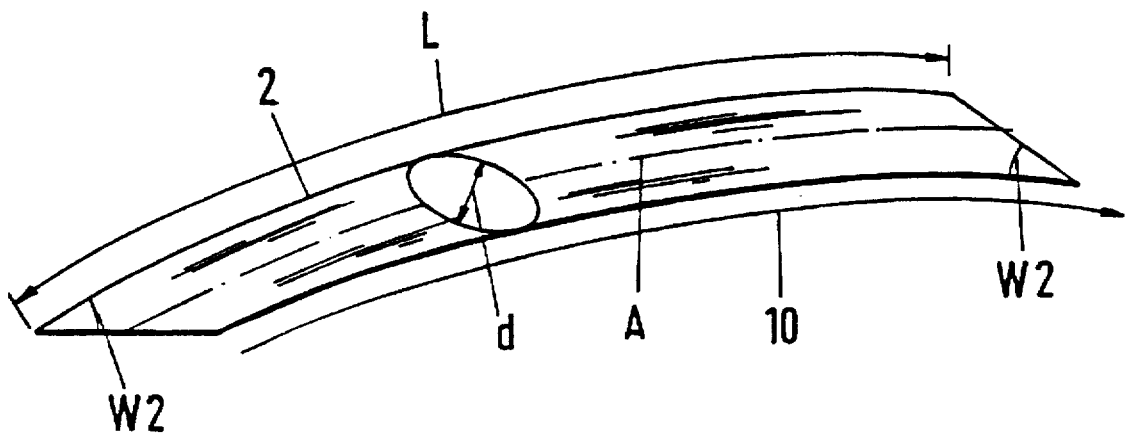
FIG. 4 shows an elongated element with oblique ends.

FIG. 4 show an elongated element 2 of which the length L is more than five times its minimum diameter d, and advantageously probably even ten or more times this diameter. The ends of the elongated element 2 are cut off obliquely or finish obliquely an angle W2 of, for example, 30°to 60° to the element axis A, with the result that the thermoplastic connection between different elongated elements in the endoprosthesis, and their compactness, can be further improved.

Figure 5:
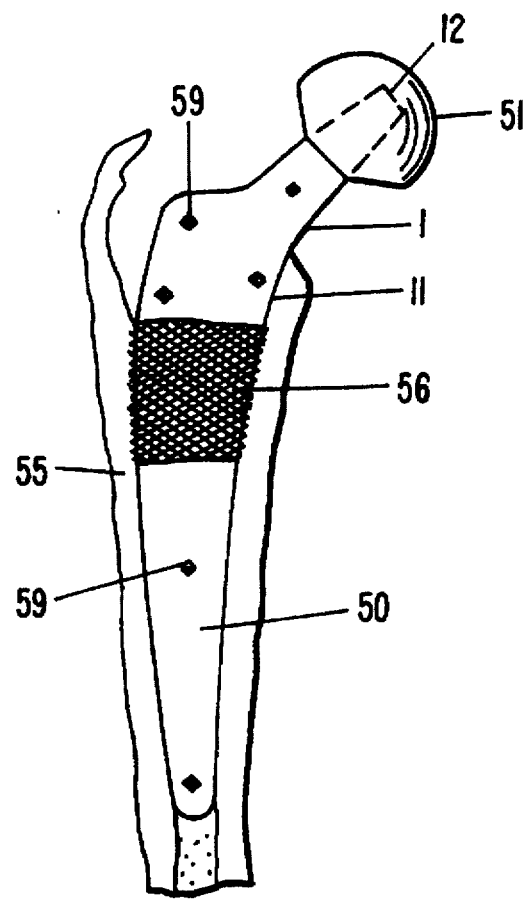
FIG. 5 shows a endoprosthesis with a stem in a tubular bone.
Figure 6:
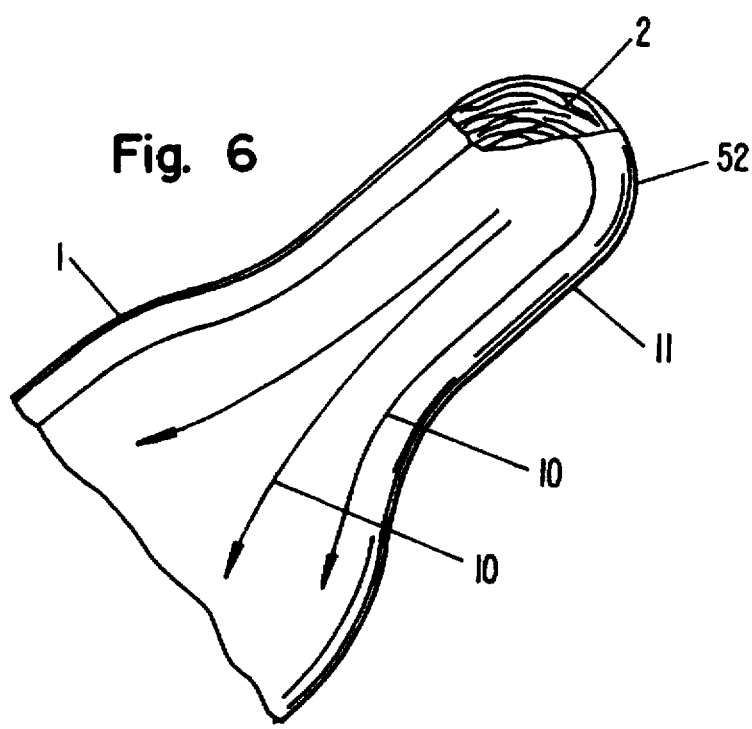
FIG. 6 shows a rounded head belonging to a endoprosthesis.

The endoprosthesis structure in accordance with the invention makes it possible to produce a great multiplicity of shapes, as the examples illustrate. FIG. 5 shows an example of an endoprosthesis with a stem 50 which is implanted in a tubular bone 55. In the upper portion of the stem 50 a metal mesh 56, for example a Sulmesh titanium mesh, is anchored thermoplastically in the surface 11 of the thermal composite material. This permits a durable and strong connection between the bone and endoprosthesis, because the bone substance grows into the metal mesh 56. At the upper end 12 a ball joint 51, for example of metal or ceramic, is put on and connected to the endoprosthesis 1. At predetermined points radiography markers 59 are incorporated in the stem 50. This makes it possible to precisely determine or monitor the position of the endoprosthesis relative to the bone 55 even after the operation. FIG. 6 shows an example with a rounded head 52 belonging to an endoprosthesis. The preferred directions 10 and consequently the elongated elements 2 here run tangentially relative to the surface 11 of the head. This produces a particularly stable surface.

Figure 7A:
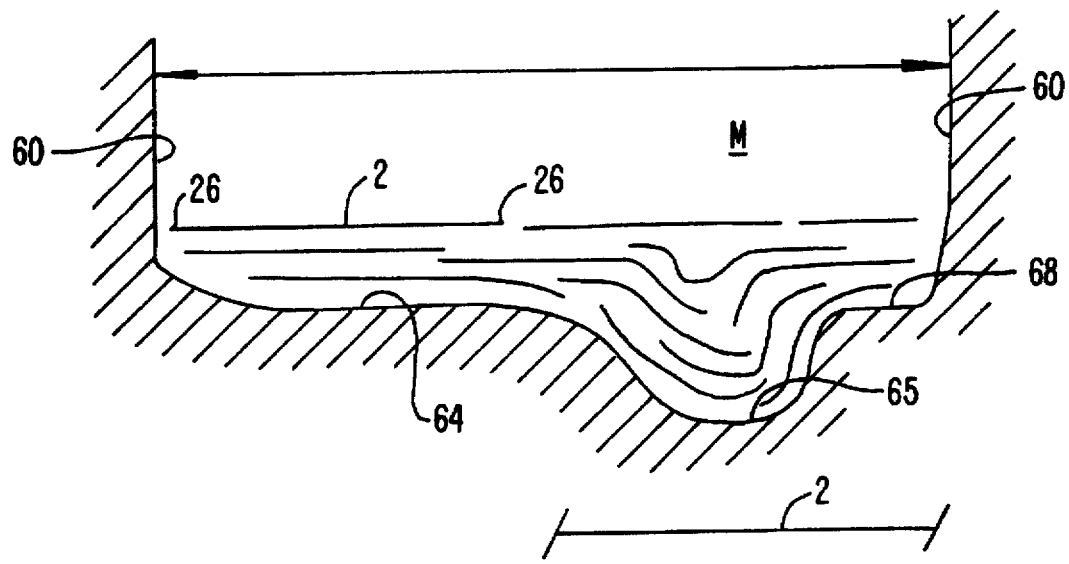
FIG. 7A shows an endoprosthesis mold in section along its major axis with the fiber sections pre-impregnated with thermoplastic material, there being illustrated exterior of the mold a fiber of an average length here shown to be less than one half the length of the mold; and, FIG. 7B shows the mold of FIG. 7A undergoing compression molding and producing relative movement between the pre-impregnated fibers to form the finished endoprosthesis of this invention, it being noted that the compression mold is also in the shape of a finished surface of the endoprosthesis.

Referring to FIG. 7A, the preferred method of manufacture of the endoprosthesis of this invention is illustrated. Mold M includes sidewalls 60 and is shown in cross-section along the major axis of the endoprosthesis to be formed. Mold M at tapering wall 64, enlarged section or head surface 65 and end section 68 is shown. Mold M has been filled with fiber sections 2, preferably pre-impregnated having tapered cut ends 26. The mold as shown is in readiness for the compression molding step shown in FIG. 7B.

Figure 7B:
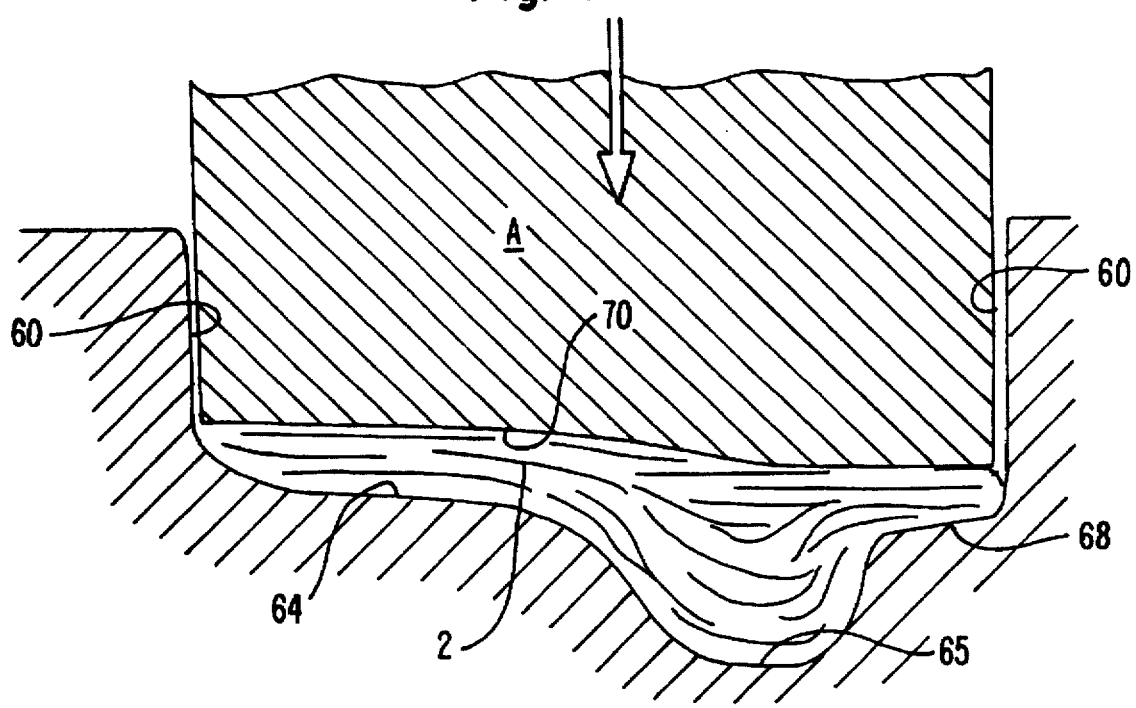

Referring to FIG. 7B, compression anvil A is compressed downward relative to fiber sections 2. Relative movement between the fiber sections 2 from the disposition shown in FIG. 7A occurs. Likewise, curing and pressing occurs.

Some specific examples can be helpful. In all cases uniform chopped fibers as previously described have been utilized. These fibers have lengths which are at least 5times the dimension of their respective diameters.

In a first example, material having 60% by volume carbon filament was pre-impregnated with 40% by volume PEEK. The chopped pre-impregnated fibers are heated up to a temperature between 380° C and 410° C. They are introduced into a mold with the general alignment previously described (fibers generally parallel to the major axis of the mold). The mold is maintained at a temperature of 220° C. Immediately upon the filling of the mold M, pressing takes place at a pressure of 800 bar for several minutes in the mold. When curing has occurred, the mold is opened and the finished endoprosthesis pushed out.

In a second example, material having 50% by volume carbon filament and 50% by volume polyamide is utilized. The chopped pre-impregnated fibers are heated up to a temperature of 220° C. The mold is maintained at 100° C. Again, compression molding occurs within a few seconds after filling of mold M at a pressure of 500 bar. The compression molding continues until curing the finished piece is removed from the mold.

It will be appreciated that the length of the pre- impregnated fibers can vary. For example, they can range from five times their respective diameters to half the length of the article formed—preferably as measured along the major axis. The fiber mixture can be uniform or varied so long as the length and diameter limitations are generally followed. For example, a mixture of uniform chopped pre-impregnated fibers could be utilized which have lengths larger than five diameters of the discrete fibers but additionally include lengths which are less than half of the main dimension.

What is claimed is:

1. A method for fabricating an endoprosthesis of compact thermoplastics composite material, the composite material being oriented along a major axis of the endoprosthesis, the method comprising the steps of:

providing a female heatable compression mold having an opening and defining a female cavity having surfaces of the endoprosthesis, the female cavity having a major axis coincident to the major axis of the endoprosthesis;

heating the female heatable compression mold to provide a heated mold;

providing a plurality of profabricated discrete and independent composite fibers and thermoplastic resin, the fibers each having a length at least five times their respective diameters and a length less than half a dimension of the endoprosthesis;

heating up a quantity of profabricated discrete and independent composite fibers and thermoplastic resin;

uniformly distributing the profabricated discrete and independent composite fibers and thermoplastic resin to fill the heated mold;

compression molding the composite fibers within the heated mold with the thermoplastic resin cured into the endoprosthesis with the composite fibers moving relative to one other during the compression molding to freely conform and cure as conformed within the heated mold into the endoprosthesis; and, removing the endoprosthesis from the mold.

2. A method for fabricating an endoprosthesis of compact thermoplastics composite material according to claim 1 and wherein the step of providing a plurality of prefabricated discrete and independent composite fibers and thermoplastic resin includes:

providing an internal core with predominately longitudinally oriented fibers oriented to the major axis of the endoprothesis and providing an enclosed cover of mutually intersecting fibers.

* * * * *